Figure 1:
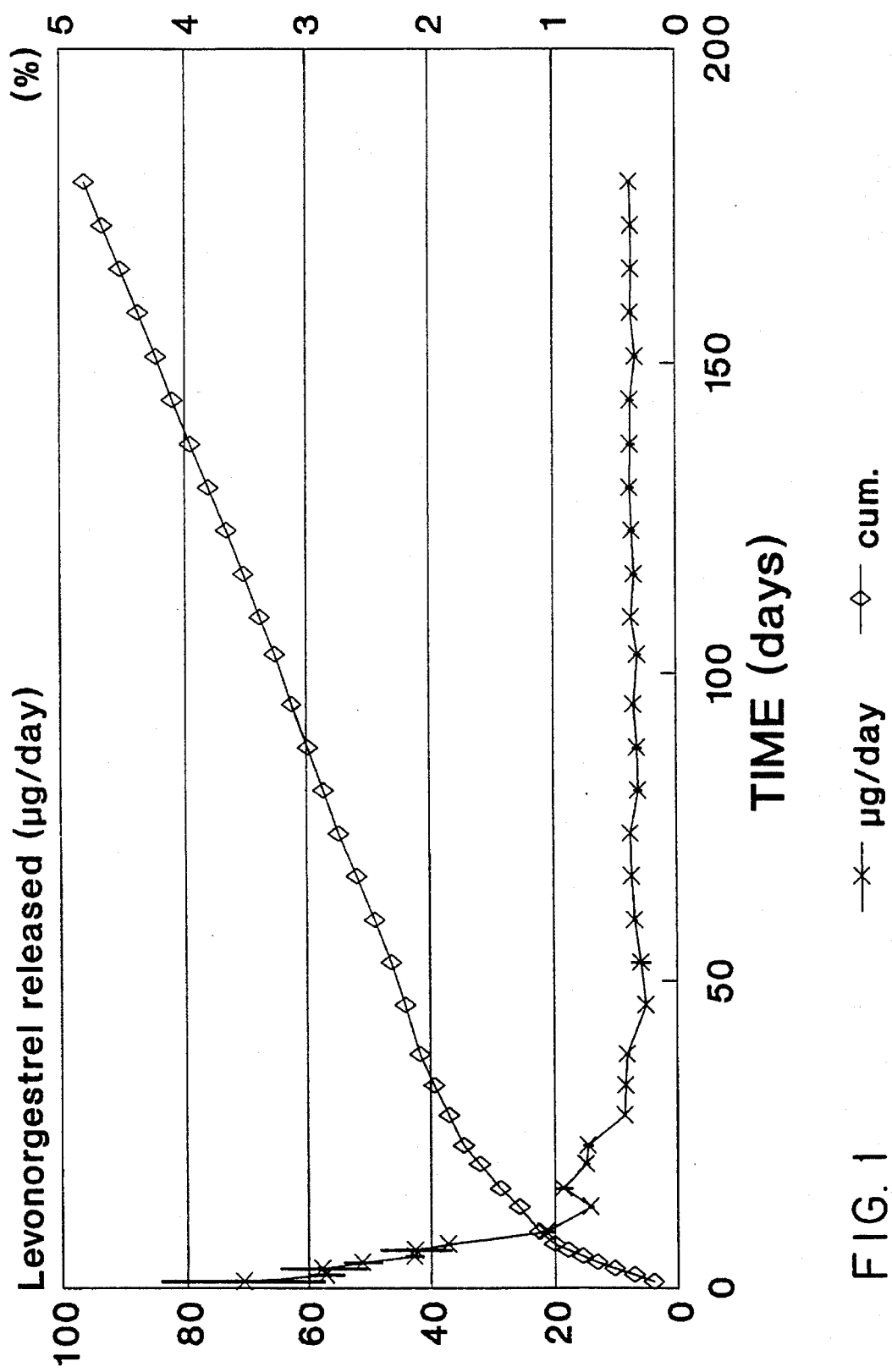

United States Patent
Törmälä et al.

[11] Patent Number: 5,620,697
[45] Date of Patent: Apr. 15, 1997

[54] METHOD FOR PREPARING MATRIX-TYPE PHARMACEUTICAL COMPOSITIONS THROUGH ULTRASONIC MEANS TO ACCOMPLISH MELTING

[75] Inventors: Pertti O. Törmälä, Tampere; Saila S. Miettinen-Lähde, Raiso, both of Finland

[73] Assignees: Orion-Yhtyma Oy, Espoo; Leiras Oy, Turku, both of Finland

[21] Appl. No.: 481,259
[22] PCT Filed: Dec. 31, 1993
[86] PCT No.: PCT/FI93/00575
§ 371 Date: Jun. 30, 1995
§ 102(e) Date: Jun. 30, 1995
[87] PCT Pub. No.: WO94/15588
PCT Pub. Date: Jul. 21, 1994

[30] Foreign Application Priority Data
Dec. 31, 1992 [GB] United Kingdom .................. 9227166

[51] Int. Cl.⁶ .................. A61F 2/02; A61K 47/30
[52] U.S. Cl. .................. 424/426; 514/772.3
[58] Field of Search .................. 424/426; 514/772.3

[56] References Cited

U.S. PATENT DOCUMENTS 4,954,298  9/1990  Yamamoto et al. .................. 264/4.6

FOREIGN PATENT DOCUMENTS 0556158  1/1991  European Pat. Off.
0406013  8/1993  European Pat. Off.

OTHER PUBLICATIONS

Kost et al., *Chemical Abstracts*, vol. 112, 1990, #62436.
Daiichi, *World Patent Abstract of Jp* 06247844, 1994.
Gombotz et al., *Chemical Abstracts*, vol. 114, 1991, #235059.
Ikada et al., *Chemical Abstracts*, vol. 116, 1991, #158947.

*Primary Examiner*—Carlos A. Azpuru
*Attorney, Agent, or Firm*—Burns, Doane, Swecker & Mathis

[57] ABSTRACT

An ultrasonic processing method by which polymer/drug composites can be quickly and efficiently molded to form matrix-type drug delivery systems is disclosed. The advantages of the method include speed and good control of the process. It also causes less degradation in polymers and/or drugs than most conventional processing methods.

17 Claims, 8 Drawing Sheets

METHOD FOR PREPARING MATRIX-TYPE PHARMACEUTICAL COMPOSITIONS THROUGH ULTRASONIC MEANS TO ACCOMPLISH MELTING

The present invention relates to a method for preparing pharmaceutical compositions using ultrasonic processing.

Matrix-type drug delivery systems, which are capable of releasing pharmaceuticals in a controlled fashion over extended periods of time are well known. Drug releasing matrices have previously been prepared by conventional polymer processing techniques, such as injection molding, extrusion or compression molding. These techniques often lead to noticeable decomposition of the active agent and/or the polymer, or are slow and cumbersome to use. The factors mainly responsible for their degradative effects are long heating times combined with mechanical stress caused by screws or other mixing devices in the machinery. The problems created by heat can be avoided by solvent casting, but this method may result in harmful solvent residues, and it is not suitable for insoluble polymers, such as polyglycolic acid (PGA).

It is an object of the present invention to provide a method for preparing drug releasing compositions eliminating the disadvantages discussed above. The object is realized by a method for preparing a drug releasing biodegradable composition comprising biodegradable polymer matrix and at least one pharmaceutical substance mixed and/or dissolved within said matrix, characterized in that using ultrasonic means a mixture of the biodegradable polymer and the pharmaceutical substance is at least partially melted.

Ultrasonic techniques are widely used in industry for the joining of thermoplastic moldings, e.g. in car and textile industry. It has now been found that ultrasonic processing can successfully be used to plasticize and mold polymeric drug delivery systems. Compared to the previously utilized methods, ultrasonic molding offers the advantage of being faster, more controllable, and substantially less destructive to the polymer and the drug.

Ultrasonic molding is based on a process in which energy from the main supply is converted by a generator into electrical vibrations in the US range (usually 20 kHz), and further transduced into mechanical vibrations of the same frequency. These mechanical vibrations are transmitted to the work pieces through a booster (transformer) and a sonotrode. The heating in the materials to be molded or joined takes place as a result of the absorption and reflection of the mechanical vibrations in the material and the interface friction of the fragments or joining surfaces.

The time required for ultrasonic processing is always very short, preferably less than 1.5 s. This fact is influential in all applications, particularly when mass-produced articles are in question. Short heating times are especially important in drug release applications, in which neither the polymer nor the active agent can withstand elevated temperatures for long periods of time.

Ultrasonic molding of polymer/drug composites is accomplished by standard ultrasonic welding equipment, provided it is supplied with a sonotrode and a mold suitable for producing of matrices of desired size and geometry. Tablet- or rod-shaped matrices, for example, are easily produced, but more complicated geometries can also be prepared.

Polymeric materials suitable for ultrasonically processed drug releasing matrices include e.g. polyorthoesters and biodegradable poly-α-hydroxy acids, such as polyglycolide (PGA), polylactides (PLA), polyhydroxybutyrate (PHB) and PHB/polyhydroxyvalerate (PHV) copolymers. Many of these materials are extremely difficult to injection mold or extrude due to their narrow melting temperature ranges. The process may, in fact, become impossible to control when the polymers have been blended with pharmaceuticals: drastic changes in the viscosity of the materials can occur within a 0.5° C. change in temperature or with time, and differences in the melting points of the constituents often result in one or more of the substances being at least partially destroyed. In ultrasonic molding these problems can largely be avoided, because the process is almost instantaneous, and because the process parameters (welding time, holding time, pressure, welding energy, welding distance, amplitude, impact speed) can be very accurately determined.

Examples of the drugs compatible with ultrasonic processing are e.g. antibiotics, polypeptides and steroid hormones. Many other classes of pharmaceuticals, the long term and/or local delivery of which is beneficial, can also be used.

Ultrasonically produced drug delivery systems can best be used as macroscopic implantable devices, such as long-term contraceptive systems placed under the skin, or as antibiotic loaded rods implanted in osteomyelitic bone. The preparation of these or other types of implants consists, in general, of mixing the polymer with the pharmaceutical substances, vacuum drying the blend, and molding it with ultrasound.

Homogenization of the polymer/drug blend can be done for example by mechanically mixing finely ground powders, by stirring the polymer powder in a drug solution, by dissolving both (all) substances in a common solvent, or by impregnating the polymer with the drug solution. Thorough vacuum drying of the materials after blending is preferred for predictable processing and release results.

Molding of the materials can be done with a standard ultrasonic welding apparatus, which is equipped with an appropriately designed sonotrode and a mold of desired size and shape. The dried substances are placed into the mold, and ultrasound is applied on them. The processing time required to plasticise and form a 0.25 g sample varies between 0.1 and 1.0 s depending on the materials in question, as well as on the pressure and amplitude (booster) used. The energies transmitted to this size of samples are approximately 50–500 Ws.

It has been found that most injection molded and extruded matrices show substantially worse and less predictable in vitro release behavior than ultrasonically prepared samples, which is due to the degradative effect of these methods on the polymers and especially to the drugs. In vitro drug release from ultrasonically molded samples is roughly equivalent to that from compression molded samples. However, variation of the results is greater in compression molded samples, and when comparing the processing techniques themselves, ultrasonic molding comes out as the easier, faster and more accurate technique.

Figure 2:
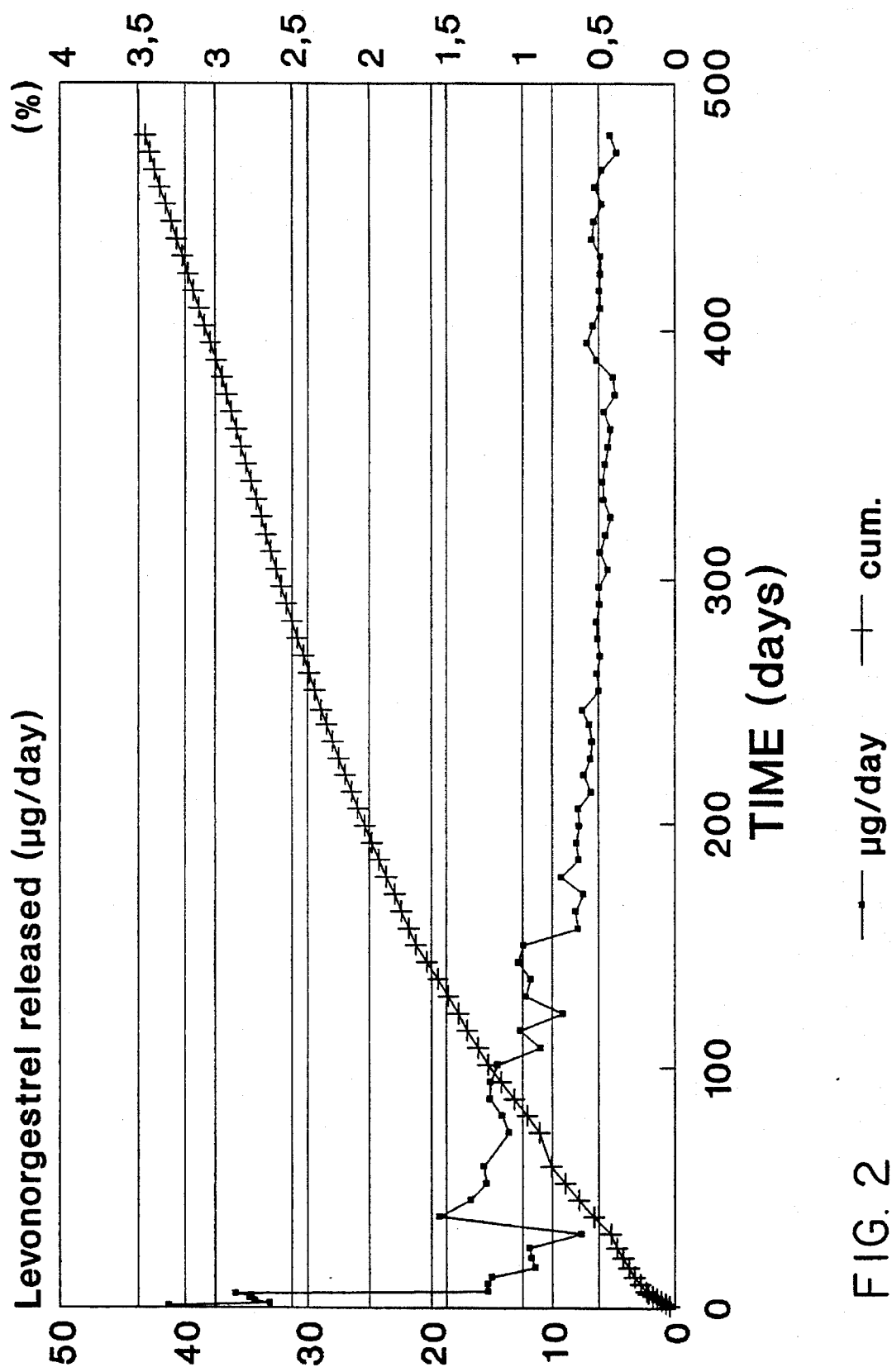
Figure 3:
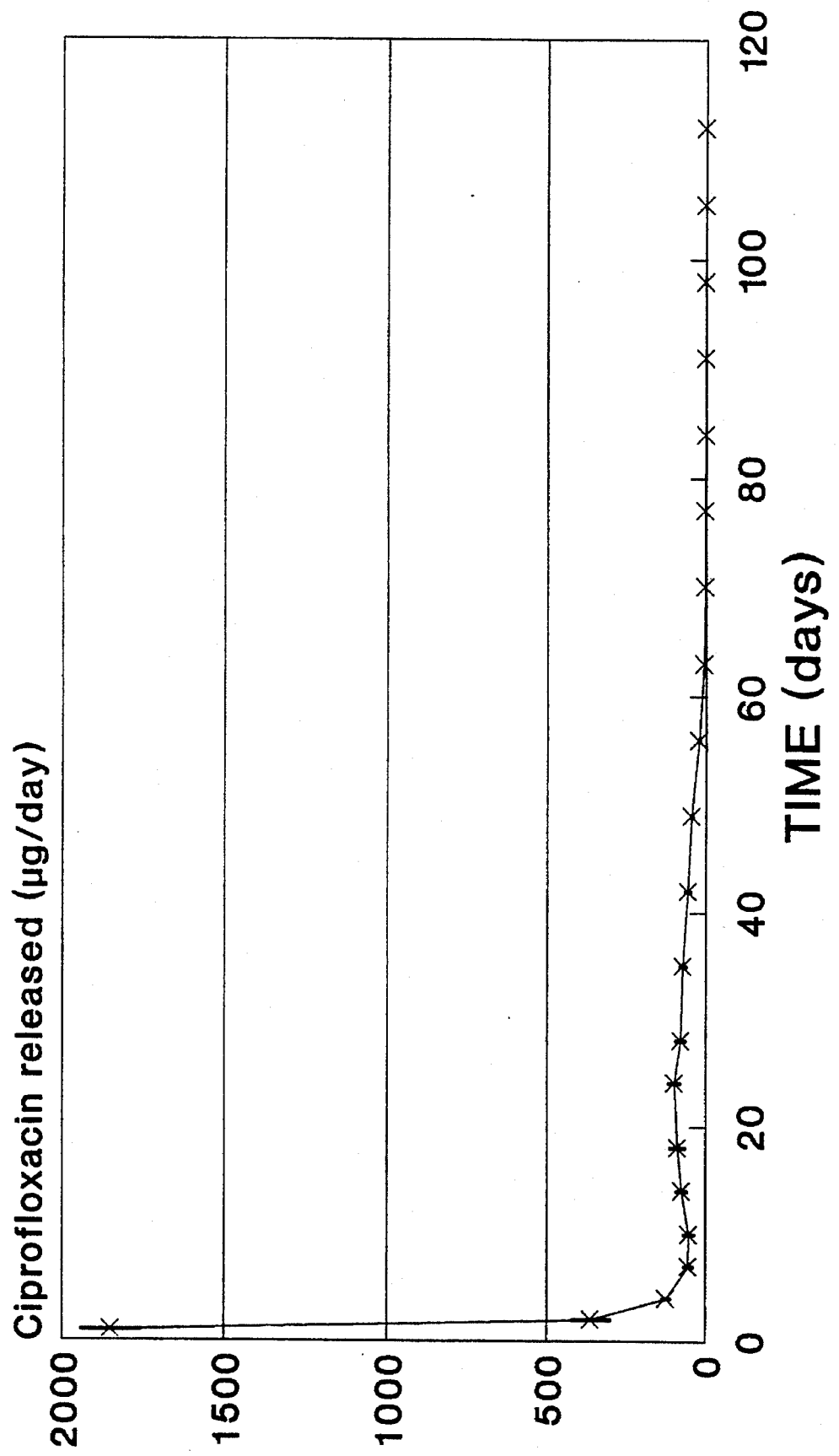
Figure 4:
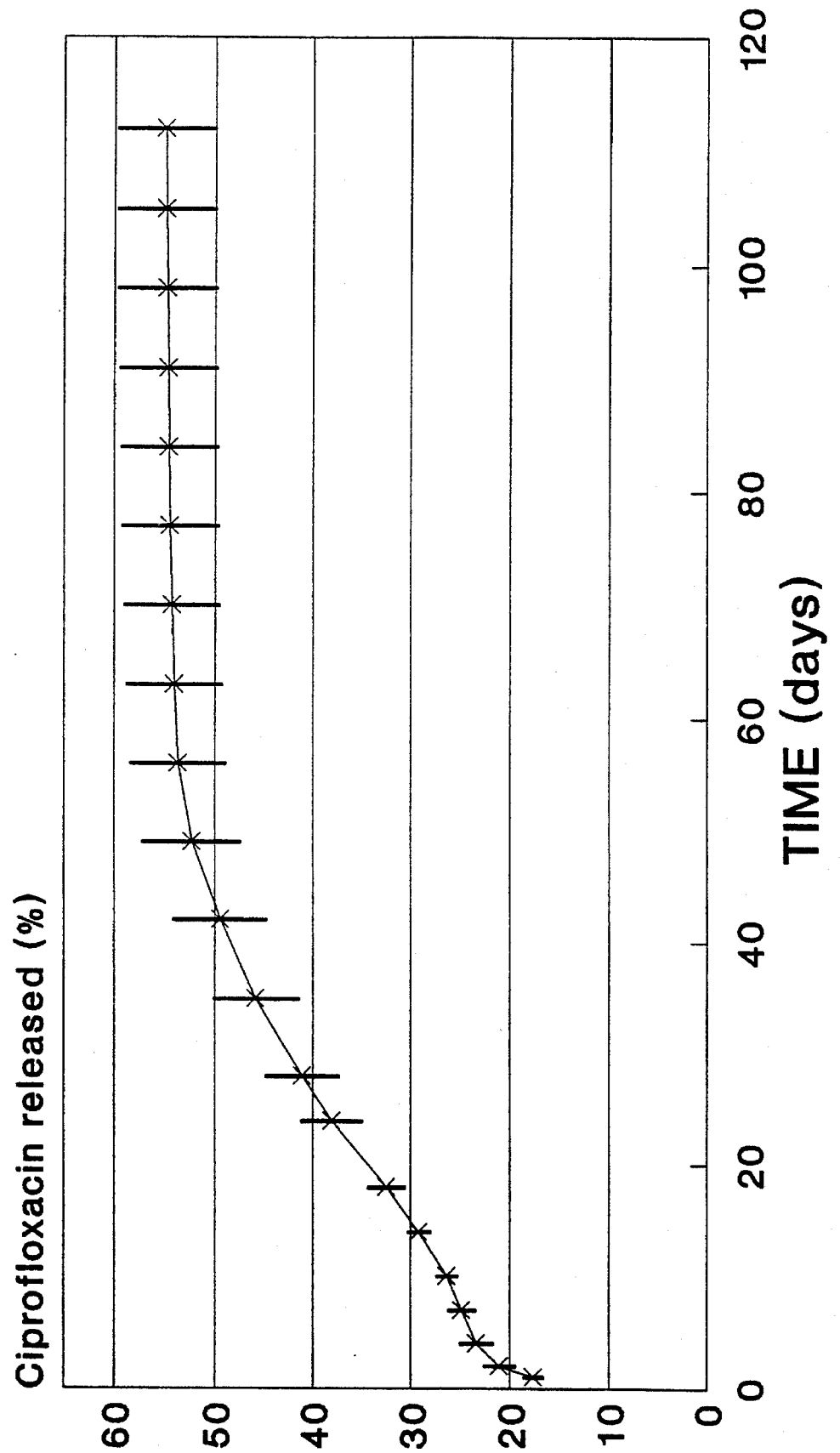
Figure 5:
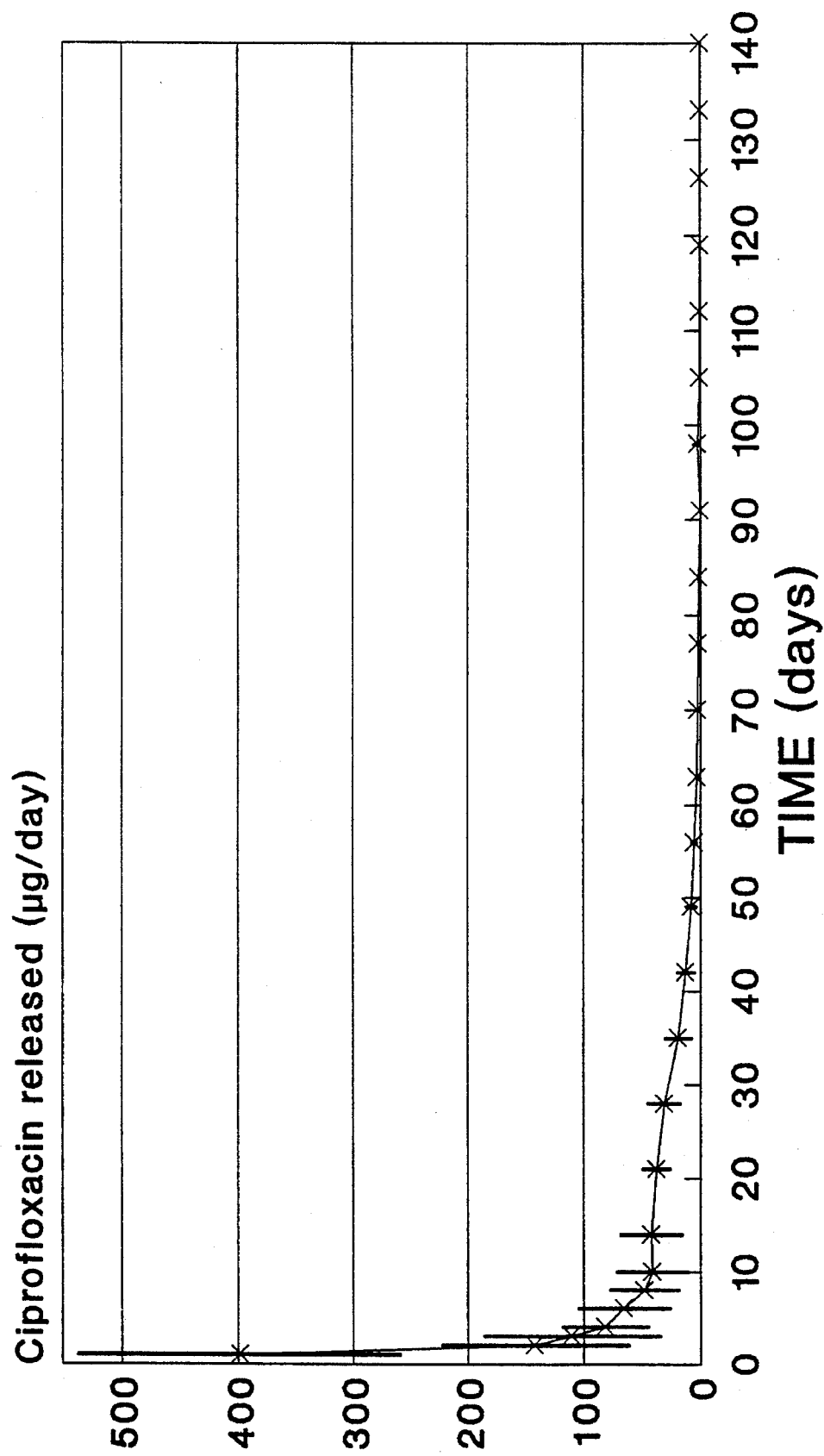
Figure 6:
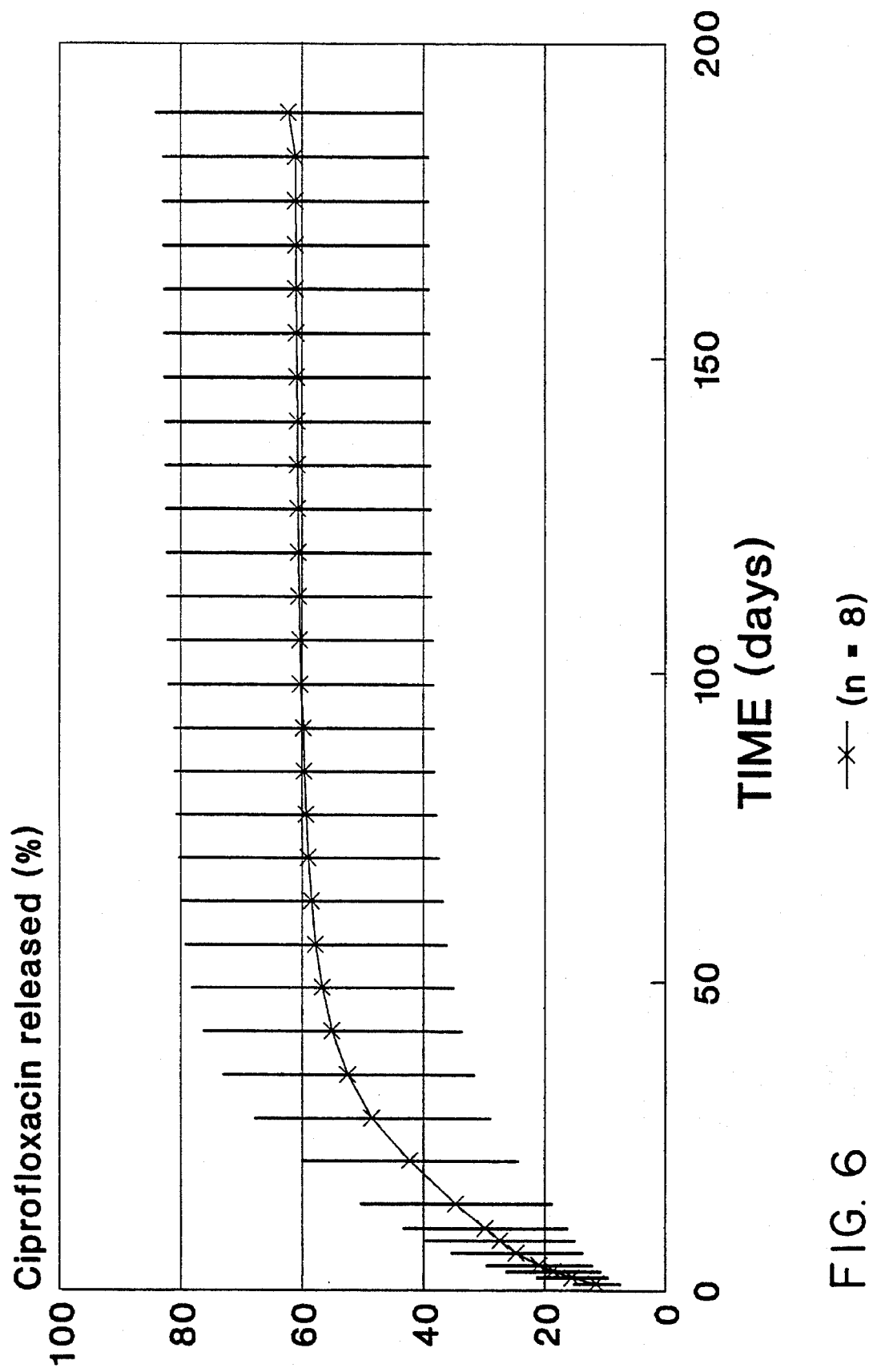
Figure 7:
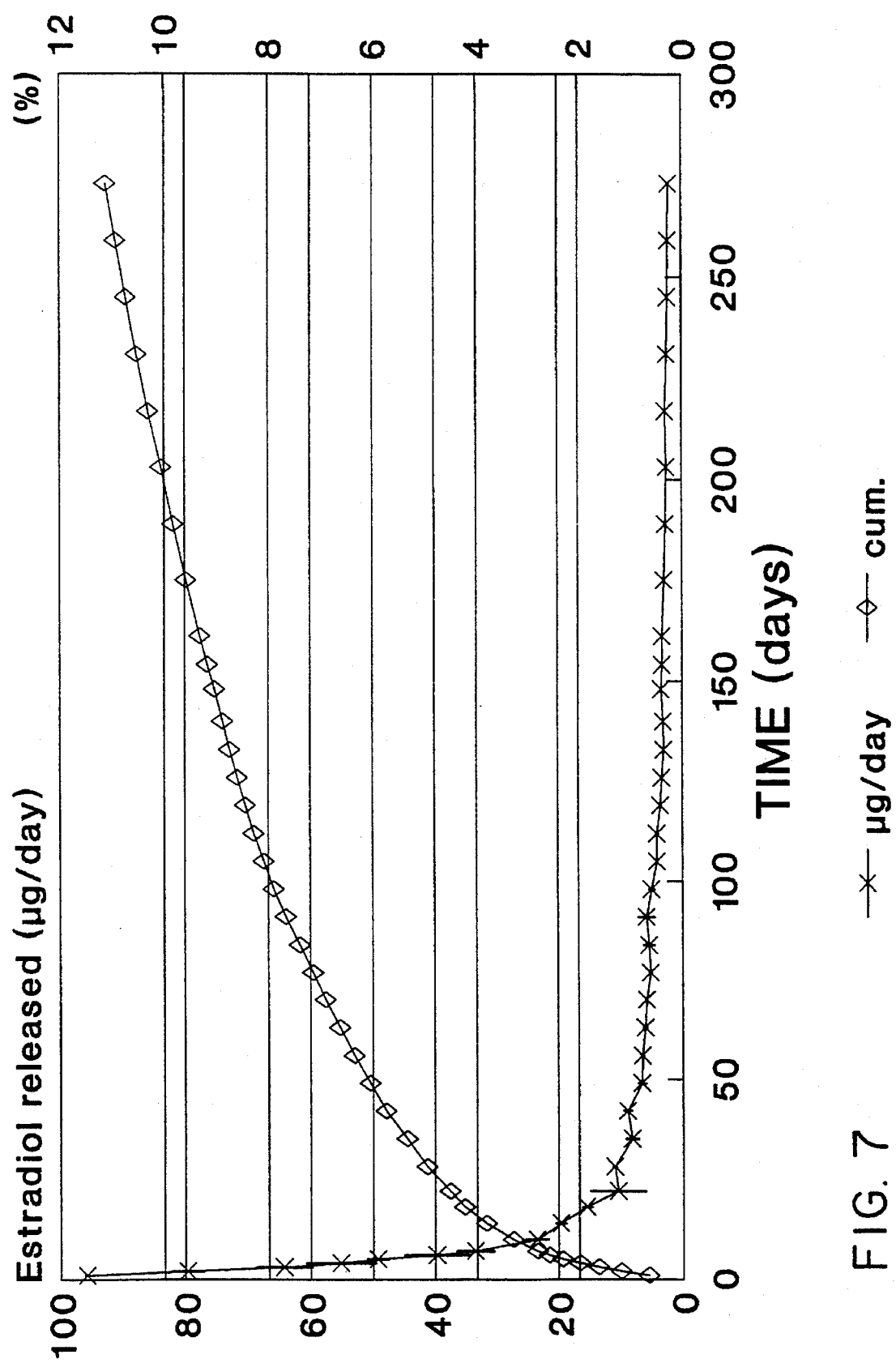
Figure 8:
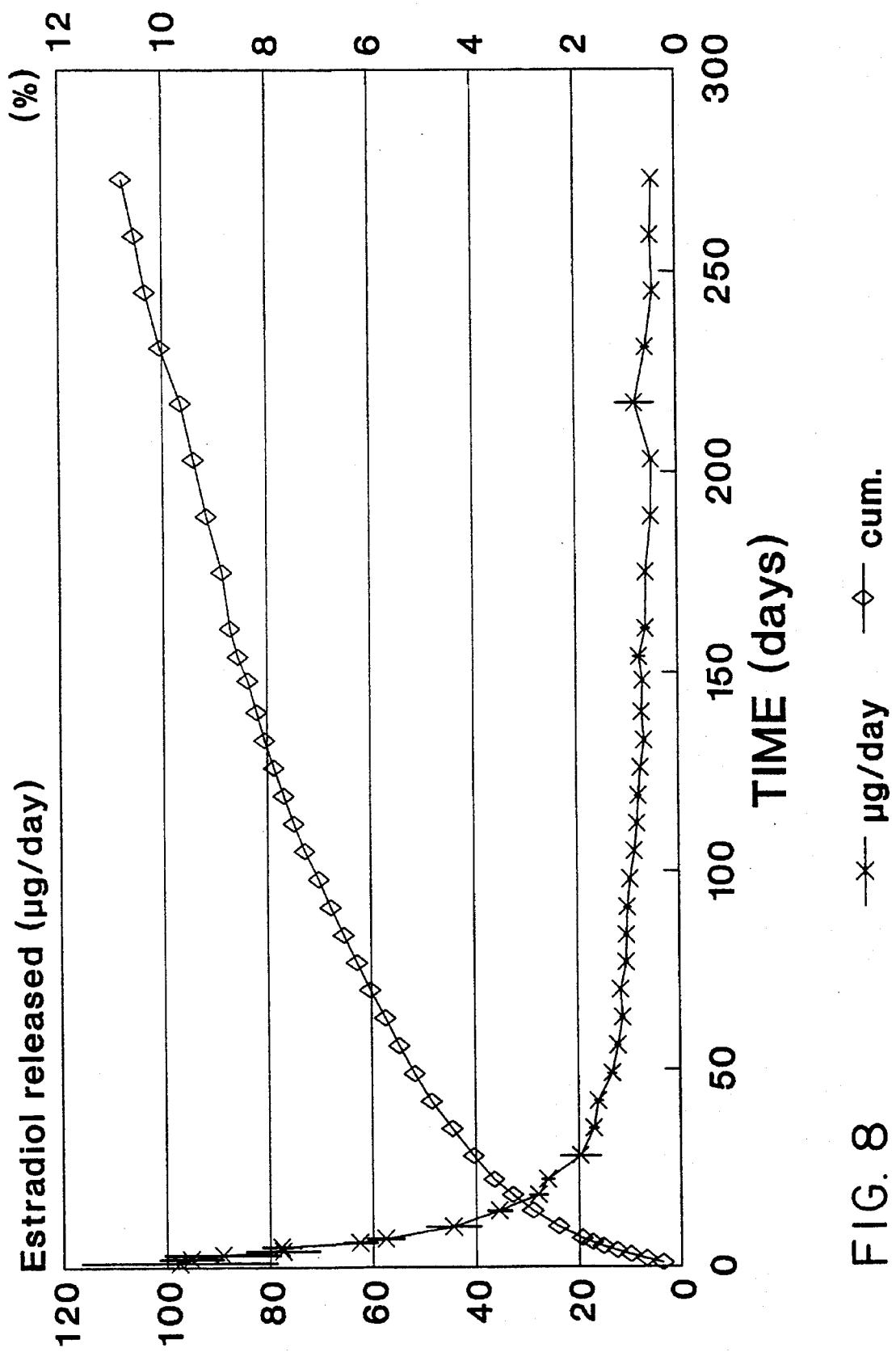

The invention is further illustrated by the following Examples, where reference is made to the accompanying drawings. In the drawings, FIG. 1 shows in vitro release of levonorgestrel from ultrasonically processed PLLA matrice, FIG. 2 shows in vitro levonorgestrel release from compression molded PLLA matrice, FIG. 3 shows in vitro ciprofloxacin release from ultrasonically molded PGA matrice, FIG. 4 shows cumulative in vitro ciprofloxacin release from ultrasonically molded PGA matrice, FIG. 5 shows in vitro ciprofloxacin release from compression molded PGA rods, FIG. 6 shows cumulative in vitro ciprofloxacin release from compression molded PGA rods, FIG. 7 shows in vitro 17-β-estradiol release from ultrasonically molded PHB/PHV slabs (7.5 wt % 17βestradiol) and FIG. 8 shows in vitro 17-β-estradiol release from ultrasonically molded PHB/PHV slabs (15wt % 17-β-estradiol)

EXAMPLE 1

Effects of injection molding and ultrasonic processing on poly-L-lactide (PLLA)

PLLA (MW 260 000) was first dried in vacuum and subsequently either ultrasonically processed or injection molded in nitrogen atmosphere. The samples produced by ultrasound were φ 11×2 mm buttons, and the duration of ultrasound application on each sample was approximately 0.3 s. The energy transmitted to the buttons was 200 Ws, and the pressure during molding 1.3 bar. Injection molding was done with a Battenfeld BA 230 apparatus, and the molded samples were shaped as rods of various sizes. Both types of samples were ground and again vacuum dried before testing.

Processing-induced changes in polymer properties and structure were assessed by melt flow index (MFI) measurements and differential scanning calorimetry (DSC). The MFI measurements, done at 180°–195° C., showed that injection molding had had a major degradative effect on PLLA, as the MFI at all temperatures had markedly increased. The increase in MFI caused by ultrasonic processing was less severe (Table 1). DCS scans showed a slight decrease in melting points in the injection molded as well as in the ultrasonically processed samples. The smaller degree of crystallinity of the ultrasonically prepared PLLA is caused by the quick cooling that follows the ultrasound application (Table 2).

TABLE 1

Melt flow index (MFI) values of PLLA

| | MFI (g/10 min) | | | |
|---|---|---|---|---|
| | 180° C. | 185° C. | 190° C. | 195° C. |
| Raw material (MW 260000) | — | 0.20 | 0.84 | 1.25 |
| Injection molded | 3.11 | 5.66 | 7.60 | 9.74 |
| Ultrasonically molded | — | 4.31 | 4.30 | 6.18 |

TABLE 2

Melting points (°C.) and degrees of crystallinity of PLLA

| | Tm (deg. C.) | Crystallinity % |
|---|---|---|
| Raw material (MW260000) | 185.7 | 63.4 |
| Injection molded | 181.8 | 61.2 |
| Ultrasonically molded | 181.1 | 38.9 | degree of crystallinity calculated from the melting enthalpy of the sample relative to that of 100% crystalline PLLA

EXAMPLE 2

Total concentration of active agents in ultrasonically processed, compression molded and injection molded matrices Ultrasonically molded samples were prepared from vacuum dried PLLA (MW 260 000)/15 wt % levonorgestrel mixture using Rinco PCS ultrasonic welding equipment. The φ 11×2 mm, button shaped samples were made using a welding time of 0.3 s, 1.3 bar and appr. 200 Ws of energy per sample. A few of the prepared samples were dissolved in chloroform, and the total concentration levonorgestrel in the solution was determined UV-spectrophotometrically at 240 nm. The levonorgestrel content of the samples was found to be close to 100% of the theoretical amount of the drug present.

A similar PLLA/15 wt % levonorgestrel mixture was compression molded into φ 20×2 mm slabs at 170°–175° C. for 5 min. The pressure applied on the samples during processing was 10 MPa. The levonorgestrel content measured from dissolved slabs was again nearly 100% of the expected.

Injection molded PLLA/15 wt % levonorgestrel samples were prepared by first melt homogenizing the dried material in a Brabender Plasticord batch mixer at 190° C., and by then injection molding it into φ 20×2 mm slabs with a laboratory scale SP-2 apparatus at 195°–200° C. In these samples, only appr. 24% of the theoretical amount of levonogestrel was found to be present after processing, which clearly shows the detrimental effect of injection molding/melt homogenization on these materials.

EXAMPLE 3.

In vitro release of levonogestrel from ultrasonically processed, compression molded and injection molded PLLA matrices The in vitro hydrolysis experiments of all samples were done in phosphate buffer (pH 7.4) at 37° C. The buffer solutions were changes periodically, and the levonorgestrel concentration in the solutions was assessed by HPLC (Merck Hitachi).

The compression molded PLLA/15% levonorgestrel matrices have released levonorgestrel fairly steadily, 10–12 µg/day, after initial burst (FIG. 2). The release has been strongly dependent on the solubility of the steroid in the buffer solution rather than on the properties of the matrix. No signs of the active agent having been destroyed during processing have been detected, however.

The release from ultrasonically processed samples (FIG. 1) has been 6–8 µg/day, after the initial burst (after about 25 days). After 180 days the total amount released has been 4.8%.

Levonorgestrel release from the injection molded samples was barely at a detectable level (<<1 µg/day) throughout most of the test period. Because of the very scant release, and also due to rapidly degrading matrices, the experiments were deemed unsuccessful and discontinued after two months of hydrolysis.

EXAMPLE 4

In vitro ciprofloxacin release from ultrasonically processed and compression molded polyglycolic acid (PGA) matrices.

Ciprofloxacin loaded PGA matrices, which can be used for the local, controlled antibiotic treatment of osteomyelitis, were prepared from ciprofloxacin impregnated Dexon 2"S" suture. The impregnated (5 wt % ciprofloxacin), vacuum dried suture was either compression molded into φ 3.2×5 mm rods or ultrasonically formed into φ 11×2 mm slabs. The compression molding was done at 200°–205° C. under 0–20 MPa pressure for 6–7 minutes. Ultrasonic processing was accomplished with a welding time of appr. 1.5 s, 1.2 bar pressure and 270–300 Ws of transmitted energy.

Ciprofloxacin release from the ultrasonically prepared samples started at 1849±93 µg/day (X±SD, N=8) and tapered down to 0.8±0.3 µg/day after 112 days (FIG. 3). The experiment was discontinued at this time, because all of the samples had degraded completely. At the completion of the hydrolysis the percentage of the antibiotic release had reached 55±5% of its theoretical amount (FIG. 4). The remaining appr. 45% had been lost during processing due to incomplete absorption into the sutures.

Hydrolysis results of the compression molded samples are presented in FIGS. 5 and 6. It can be seen that the ciprofloxacin release from the samples was comparable to that from ultrasonically processed samples, especially considering the differences in the size and shape of the samples. However, variation between individual samples was noticeably greater in the compression molded rods. Also, the compression molding process takes 20–30 min/sample, whereas the ultrasonic forming can be done in less than two seconds.

EXAMPLE 5

Ultrasonically molded PHB/PHV / 17-β-estradiol samples

Micronized estradiol and PHB/PHV powder (particle size<350 µm) were mechanically mixed in the ratios of 7.5:92.5 and 15:85. The homogenized mixture was vacuum dried at 30° C. for 3 days and then ultrasonically molded into φ 11×2 mm slabs. The processing parameters included the welding time of 0.118–0.128 s, 5.0 s holding time, 1.1 bar pressure and 53 Ws of welding energy. Some of the slabs were dissolved in chloroform, and the total estradiol content of the samples was determined from the solution by a Perkin Elmer Lambda 17 UV/VIS-Spectrophotometer at 280 nm. The amount of estradiol found was close to 100% of the theoretical.

In vitro hydrolysis experiments of PHB/PHV / 17-β-estradiol slabs were done in phosphate buffer (pH 7.4, 37° C.). The buffer solution was periodically changed, and the estradiol concentration in the solution was assessed by HPLC (Merck Hitachi). The results show a nearly first order release, which is typical for matrix-type drug delivery systems (FIG. 7 and 8).

FIG. 7 (mixing ratio 7.5:92.5) shows that the release has been 6–11 µg/day during the period of 20–70 days, after the initial burst. During the period of 120–290 days the release has been about 2–4 µg/day. After 290 days the total amount released has been 11.5%.

FIG. 8 (mixing ratio 15:85) shows that the release has been 10–13 µg/day during the period of 50–100 days, after the initial burst. During the period of 100–230 days the release has been about 4.5–10 µg/day. After 230 days the total amount released has been 10.5%.

We claim:

1. A method for preparing a matrix-type solid drug releasing biodegradable composition comprising a solid biodegradable polymer matrix and at least one solid pharmaceutical substance mixed and/or dissolved within said matrix, comprising the steps of subjecting said biodegradable polymer matrix and said at least one pharmaceutical substance while in admixture as solids to the action of ultrasonic means whereby said mixture is at least partially melted, and thereafter cooling said mixture to form said matrix-type drug releasing biodegradable composition.

2. A method according to claim 1 characterized in that the mixture of biodegradable polymer and pharmaceutical substance is vacuum dried before the ultrasonical melting.

3. A method according to claim 1 characterized in that the biodegradable polymer matrix comprises a polyorthoester, a polylactide or a poly-α-hydroxy acid.

4. A method according to claim 3 characterized in that the biodegradable polymer matrix comprises polyglycolide (PGA), poly-L-lactide (PLLA), polyhydroxybutyrate (PHB) or a PHB/polyhydroxyvalerate (PHV) copolymer.

5. A method according to claim 1 characterized in that the pharmaceutical substance is an antibiotic, a steroid hormone or a polypeptide.

6. A method according to claim 5 characterized in that the pharmaceutical substance is levonorgestrel, ciprofloxacin or 17-β-estradiol.

7. A matrix-type solid drug releasing biodegradable composition comprising biodegradable polymer matrix and at least one pharmaceutical substance mixed and/or dissolved within said matrix prepared according to the method of claim 1.

8. A matrix-type solid drug releasing biodegradable composition according to claim 7 characterized in that the composition is capable of being implanted in the human or animal body.

9. A method according to claim 2 characterized in that the biodegradable polymer matrix comprises a polyorthoester, a polylactide or a poly-α-hydroxy acid.

10. A method according to claim 2 characterized in that the pharmaceutical substance is an antibiotic, a steroid hormone or a polypeptide.

11. A method according to claim 3 characterized in that the pharmaceutical substance is an antibiotic, a steroid hormone or a polypeptide.

12. A method according to claim 4 characterized in that the pharmaceutical substance is an antibiotic, a steroid hormone or a polypeptide.

13. A matrix-type solid drug releasing biodegradable composition comprising biodegradable polymer matrix and at least one pharmaceutical substance mixed and/or dissolved within said matrix characterized in that said composition is prepared according to the method of claim 2.

14. A matrix-type solid drug releasing biodegradable composition comprising biodegradable polymer matrix and at least one pharmaceutical substance mixed and/or dissolved within said matrix characterized in that said composition is prepared according to the method of claim 3.

15. A matrix-type solid drug releasing biodegradable composition comprising biodegradable polymer matrix and at least one pharmaceutical substance mixed and/or dissolved within said matrix characterized in that said composition is prepared according to the method of claim 4.

16. A matrix-type solid drug releasing biodegradable composition comprising biodegradable polymer matrix and at least one pharmaceutical substance mixed and/or dissolved within said matrix characterized in that said composition is prepared according to the method of claim 5.

17. A matrix-type solid drug releasing biodegradable composition comprising biodegradable polymer matrix and at least one pharmaceutical substance mixed and/or dissolved within said matrix prepared according to the method of claim 6.

* * * * *